United States Patent [19]

Kadin

[11] 4,342,781
[45] * Aug. 3, 1982

[54] DIPHENYLPROPENAMIDES AS SRS-A ANTAGONISTS

[75] Inventor: Saul B. Kadin, New London, Conn.

[73] Assignee: Pfizer Inc., New York, N.Y.

[*] Notice: The portion of the term of this patent subsequent to Oct. 20, 1998, has been disclaimed.

[21] Appl. No.: 268,439

[22] Filed: May 29, 1981

[51] Int. Cl.³ .................. A61K 31/24; C07C 101/453
[52] U.S. Cl. ..................................... 424/319; 562/442
[58] Field of Search .......................... 560/37; 562/442; 424/309, 319

[56] References Cited

U.S. PATENT DOCUMENTS

| | | | |
|---|---|---|---|
| 3,993,679 | 11/1976 | Hall et al. | 560/37 |
| 4,036,837 | 7/1977 | Sellstedt et al. | 560/37 |
| 4,238,506 | 12/1980 | Stach et al. | 562/442 |
| 4,296,129 | 10/1981 | Kadin | 560/37 |

*Primary Examiner*—Natalie Trousof
*Assistant Examiner*—James H. Reamer
*Attorney, Agent, or Firm*—Charles J. Knuth; Albert E. Frost; J. Trevor Lumb

[57] ABSTRACT

Certain new diphenylpropenamides having a carboxyalkanamido or a carboxyalkenamido group on one of the phenyl rings and their use for antagonizing the spasmogenic activity of the slow-reacting substance of anaphylaxis (SRS-A) in a human subject. In particular, the compounds of the invention are useful for preventing and treating certain obstructive airways diseases, notably allergic bronchial asthma, allergic rhinitis and certain skin disorders, in human subjects.

17 Claims, No Drawings

DIPHENYLPROPENAMIDES AS SRS-A ANTAGONISTS

BACKGROUND OF THE INVENTION

This invention relates to new chemical compounds, and more particularly it relates to derivatives of 2,3-diphenylpropenamide and 3,3-diphenylpropenamide. Said derivatives are further substituted on the nitrogen atom by an alkyl or cycloalkyl group, and on one of the phenyl groups by a carboxyalkanamido or carboxyalkenamido group. These compounds are useful as antagonists of the slow-reacting substance of anaphylaxis (SRS-A).

It is known that certain substances, known as mediators of anaphylaxis, play an important role in inducing an allergic reaction, such as bronchospastic attack or allergic rhinitis, in a human subject. Two examples of such mediators are histamine and the slow-reacting substance of anaphylaxis (SRS-A), the latter substance being a very important mediator in allergic bronchial asthma. SRS-A is a substance which is synthesized and released in or near target tissues, in a sensitive (allergic) human subject, shortly after challenge with the appropriate antigen. The human bronchus is particularly sensitive to SRS-A.

Rational approaches to drug therapy to prevent, remove or ameliorate the symptoms of allergic reactions have focussed on either blocking the release of mediators of anaphylaxis, or, on the other hand, on antagonizing their effects. Disodium cromoglycate (The Merck Index, Merck & Co., Inc., Rahway, New Jersey, 9th Edition, 1976, 2585) is a drug which has recently been introduced and which blocks the release of mediators of anaphylaxis, and commercially available drugs which antagonize histamine (antihistamines) are well-known (e.g. methapyrilene, diphenhydramine, chlorpheniramine). Conversely, there is a paucity of substances known which antagonize SRS-A, and none of them is used in clinical practice today. One agent has been widely studied (FPL 55712-*Agents and Actions*, 9, 133 [1979]).

SUMMARY OF THE INVENTION

This invention provides novel diphenylpropenamide compounds of the formula

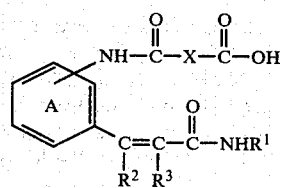

and the pharmaceutically-acceptable salts thereof;
wherein $R^1$ is selected from the group consisting of alkyl having from 8 to 15 carbons and cycloalkyl having from 6 to 12 carbons;
X is selected from the group consisting of cis-vinylene, ethylene and propylene;
and $R^2$ and $R^3$ are each selected from the group consisting of hydrogen and phenyl;
with the proviso that $R^2$ and $R^3$ must always be different.

When $R^1$ is an alkyl group, it can be straight-chain or branched-chain.

This invention also provides a method of antagonizing the spasmogenic activity of the slow-reacting substance of anaphylaxis (SRS-A) in a human subject, which comprises administering to said subject an effective amount of a compound of the formula I, or a pharmaceutically-acceptable salt thereof. The compounds of formula I are antagonists of the effects of slow-reacting substance of anaphylaxis (SRS-A), and they are useful therefore for preventing and treating certain obstructive airways diseases, notably allergic bronchial asthma, allergic rhinitis and certain skin disorders in human subjects.

Still further, this invention provides pharmaceutical compositions, suitable for administration to a human subject, which comprise a pharmaceutically-acceptable carrier and a compound of the formula I, or a pharmaceutically-acceptable salt thereof.

A first preferred group of compounds of this invention is the group of compounds of formula I, wherein $R^3$ is phenyl, and the phenyl ring A and the $CONHR^1$ group have a trans relationship across the double bond. Within this first preferred group, especially preferred compounds are those in which $R^1$ is said alkyl and X is cis-vinylene.

A second preferred group of compounds of this invention is the group of compounds of formula I, wherein $R^2$ is phenyl and the phenyl ring A and the $CONHR^1$ group have a trans relationship across the double bond. Within this second preferred group, especially preferred compounds are those in which $R^1$ is said alkyl and X is cis-vinylene.

DETAILED DESCRIPTION OF THE INVENTION

In this specification, the compounds of formula I, and several of the intermediates leading thereto, are named as derivatives of 2,3-diphenylpropenamide and 3,3-diphenylpropenamide, which have structures II and III, respectively, viz:

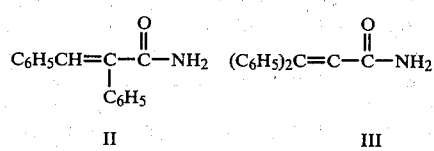

Propenoic acid refers to the carboxylic acid of the formula $CH_2=CH-COOH$, and propenoyl chloride is the derived acid chloride, $CH_2=CH-COCl$. The term "propenamido" refers to the radical $-NH-CO-CH=CH_2$, and the terms "propanamido" and "butanamido" refer to the radicals $-NH-CO-CH_2-CH_3$ and $-NH-CO-CH_2-CH_2-CH_3$, respectively.

When $R^1$ is an alkyl group, it can be straight-chain or branched-chain. However, in this specification, when the $R^1$ group is an alkyl group is is named according to the system of the Chemical Abstracts Service of the American Chemical Society. This means that within a given name each individual term denotes a straight-chain radical, having the free valency at the 1-position. For example decyl denotes the group $CH_3(CH_2)_8CH_2-$, the group $(CH_3CH_2CH_2CH_2CH_2)_2CH-$ is named 1-pentylhexyl and the group $(CH_3)_2CHCH_2CH_2CH_2CH_2CH_2-$ is named 6-methylheptyl.

The diphenylpropenamide compounds of formula I can be prepared by reaction of the appropriate amine of the formula

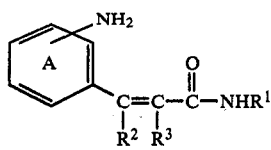
(IV)

with a cyclic anhydride selected from the group consisting of maleic anhydride, succinic anhydride and glutaric anhydride. The reaction is conveniently carried out by heating substantially equimolar quantities of the reagents in a reaction-inert solvent. A wide variety of solvents can be used for this purpose. The major requirements for such a solvent are that it substantially dissolves at least one of the reactants, it does not adversely interact with either of the reactants or the product, and the product can be recovered from it at the end of the reaction. Typical solvents which can be used are hydrocarbons, such as cyclohexane, decalin, tetralin, benzene, toluene and xylene; ethers such as 1,2-dimethoxyethane and dioxane; ketones, such as methyl isobutyl ketone and cyclohexanone; low molecular weight esters, such as ethyl acetate and butyl acetate; alkanols, such as methanol, ethanol and isopropanol; and mixtures of these solvents. The reaction is usually conducted at a temperature in the range from about 60° to about 150° C., and preferably from about 80° to 120° C. At about 90° C. the reaction is often complete within a few minutes, although in some instances it is necessary to continue the reaction for up to two hours. After the reaction is substantially complete, the compound of formula I is recovered by conventional techniques. For example, if the compound of formula I is out of solution it can be recovered by filtration; otherwise the solvent can be removed by evaporation.

Alternatively, the compound of formula I can be obtained by contacting substantially equimolar quantities of a compound of formula IV and one of the aforesaid cyclic anhydrides, at elevated temperature, in the molten state. Temperatures in the range from about 60° to about 150° C. are commonly used, with temperatures from about 80° to 120° C. being preferred. At about 90° C., the reaction is often complete within a few minutes although in some instances it is necessary to continue the reaction for up to two hours. At the end of the reaction, the product can be recovered by conventional methods. One convenient method involves cooling the reaction medium and then adding about a 10-fold excess of a solvent in which the product is only slightly soluble but in which the starting materials are readily soluble. The product is recovered by filtration. The particular solvent which is used for this purpose will vary according to the precise structure of the product, but an appropriate solvent will be chosen readily by one skilled in the art. Lower alkanols, such as methanol, ethanol and isopropanol, and low molecular weight esters, such as ethyl acetate, are commonly used.

A compound of formula I can be purified by conventional means, e.g. chromatography and/or recrystallization from an appropriate solvent.

The compounds of formula IV are obtained by reduction of the corresponding nitro compound of the formula

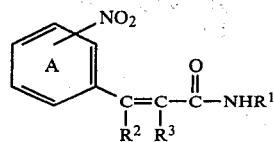
(V)

A convenient way of carrying out this reduction is to use iron in glacial acetic acid. Thus, in one method, the compound of formula V is dissolved in glacial acetic acid, the solution is heated to 85°-90° C., and then an approximately equal weight of iron powder is added portionwise with stirring, during about 10 to 15 minutes. The reaction mixture is stirred an additional 15 minutes and then the solids are removed by filtration. The solids are washed with acetic acid, and then the combined acetic acid solutions are evaporated to give the compound of formula IV. In many instances, the compound of formula IV is sufficiently pure in its crude state for reaction with the appropriate cyclic anhydride. However, it can be purified by conventional techniques such as chromatography and/or recrystallization, if desired.

The compounds of formula V can be obtained from the corresponding compound of the formula

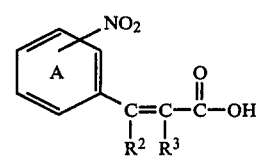
(VI)

Conversion of a compound of the formula VI into a compound of the formula V involves activation of the carboxy group followed by reaction with the appropriate amine of formula $R^1$-$NH_2$.

One convenient way of activating the carboxy group in a compound of formula VI involves conversion into the corresponding acid chloride. This is normally carried out by heating the acid with a slight excess of thionyl chloride, in benzene, at reflux temperature, for about one hour. Removal of all volatile materials by evaporation in vacuo then affords the acid chloride in essentially quantitative yield. In most instances the acid chloride is sufficiently pure for direct reaction with the amine of formula $R^1$-$NH_2$; however, it can be purified further by recrystallization from a solvent such as carbon tetrachloride, if desired.

Alternatively, the acid chloride of a compound of formula VI can be prepared by heating the acid with phosphorus trichloride and a small amount of N,N-dimethylformamide, in toluene, according to standard procedures.

Reaction of the acid chloride of a compound of formula VI with an amine of formula $R^1$-$NH_2$ is normally accomplished by dissolving the amine in a reaction-inert organic solvent such as tetrahydrofuran, cooling the solution to about 0° C., and then adding a solution of about 0.5 equivalents of the acid chloride, in a small volume of the reaction-inert solvent, dropwise, with stirring, during about 10 to 20 minutes. At a temperature of about 0° to 25° C., the reaction takes about one to about four hours substantially to reach completion. At the end of the reaction, the reaction medium is partitioned between water and a volatile, water-immiscible, organic solvent. The organic solvent is removed, washed with water at pH 7.0 and with water at pH 3.5, and then dried. Removal of the solvent by evaporation in vacuo affords the compound of formula V.

A second convenient way of activating the carboxy group in a compound of the formula VI involves formation of a mixed anhydride. Mixed anhydride formation entails suspending or dissolving a carboxylate salt (e.g. the triethylamine salt) in a reaction-inert organic solvent (e.g. dichloromethane) and then adding about one molar equivalent of a hindered alkanoyl chloride (e.g. pivaloyl chloride) or a lower-alkyl chloroformate (e.g. ethyl chloroformate). The reaction is usually carried out at about 0° C., and it normally takes about 20 minutes to one hour to reach completion. Although the mixed anhydride can be isolated by solvent evaporation, it is usual simply to use it in situ for reaction with the amine of formula $R^1$-$NH_2$. In this case a solution of about one molar equivalent of the amine is added to the mixed anhydride solution, dropwise, at about 0° C. The reaction is allowed to proceed for about 30 minutes to one hour at about 0° to 25° C. If a water-immiscible solvent has been used, the product is isolated by washing the solvent with 1 N potassium hydroxide, 1 N hydrochloric acid, water and saturated sodium chloride solution. The solution is then dried and evaporated in vacuo to give the compound of formula V. If a water-miscible solvent has been used, the product can be isolated by removing the solvent by evaporation in vacuo, replacing it with a water-immiscible solvent, and then proceding as described above.

The compounds of formula VI, wherein $R^2$ is hydrogen and $R^3$ is phenyl, are prepared by condensation of the appropriate nitrobenzaldehyde with phenylacetic acid, according to standard procedures.

The compounds of formula VI, wherein $R^2$ is phenyl and $R^3$ is hydrogen, are prepared by condensation of the appropriate nitrobenzophenone with diethyl ethoxycarbonylmethylphosphonate, followed by basic hydrolysis of the ethyl ester grouping, according to standard procedures.

As will be appreciated by one skilled in the art, a compound of the formula I can exist in one of two geometrical isomers, by virtue of the presence of the double bond to which the two phenyl groups and the $CONHR^1$ group are attached. In one isomer, the phenyl group A and the group $CONHR^1$ are on opposite sides of the double bond from each other, and in this specification this isomer is termed the trans-isomer. In the other isomer, the phenyl group A and the group $CONHR^1$ are on the same side of the double bond as each other, and in this specification this isomer is termed the cis-isomer. Both isomers, and mixtures thereof, are within the scope of this invention; however, the trans-isomers are preferred.

In like manner, the compounds of formulae IV, V and VI can exist as two geometrical isomers. In the trans-isomers, the phenyl ring A and the $CONHR^1$ or COOH group are on opposite sides of the double bond; in the cis-isomers, the phenyl ring A and the $CONHR^1$ or COOH group are on the same side of the double bond.

If it is desired to prepare a trans-isomer of the formula I, the synthetic sequence VI to V to IV to I can be carried out starting with the trans-isomer of a compound of formula VI. Conversely, operation of the synthetic scheme VI to V to IV to I, starting with the cis-isomer of a compound of formula VI leads to the cis-isomer of formula I. Additionally, if the synthetic sequence VI to V to IV to I is started using a mixture of isomers, separation can be effected at various stages in the synthetic sequence. Standard separation techniques such as recrystallization and/or chromatography can be used.

The compounds of the formula I are acidic and they form base salts. All such base salts are within the scope of this invention. They can be prepared by conventional methods for carboxylic acid compounds. For example, they can be prepared readily and conveniently simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, or by evaporation of the solvent, as appropriate, or, in the case of aqueous solutions, by lyophilization. Basic agents suitably employed in salt formation belong to both the organic and inorganic types, and they include ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazobicyclo[4.3.0]non-5-ene; hydroxides, such as sodium hydroxide; alkoxides, such as sodium methoxide and potassium methoxide; hydrides, such as calcium hydride and sodium hydride; and carbonates, such as potassium carbonate and sodium carbonate.

As indicated hereinbefore, the compounds of formula I are of value as antagonists of the slow-reacting substance of anaphylaxis (SRS-A). This activity can be detected and evaluated by methods known in the art. In one method, the ability of a compound of formula I to antagonize SRS-A induced contractions in isolated guinea pig ileal muscle is measured. Terminal ileum segments, 2.5 cm. long, are removed from Reed-Willet guinea pigs, 350–450 g., and suspended in 10 ml. muscle baths containing Tyrode's solution (NaCl-136.9 mM, KCl-2.68 mM, $CaCl_2$-1.8 mM, $NaH_2PO_4$-0.42 mM, $MgCl_2$-2.0 mM, $NaHCO_3$-11.9 mM, glucose-5.5 mM) saturated with 95% $O_2$-5% $CO_2$ and maintained at 38° C. The tissue is attached by silk thread to a Statham force displacement transducer (FT 0.03) under 2 g. tension and muscle activity is recorded via a Grass Model 5 polygraph. For initial testing submaximal contractions to SRS-A (ca. 1 unit/ml.) are obtained in a total of six preparations (three from each of two animals). Each antagonist is added to all baths one minute prior to the addition of SRS-A at a concentration of $10^{-4}$ M, and the percentage inhibition of contraction is measured.

The ability of the compounds of formula I to antagonize the effects of SRS-A makes them useful for inhibiting the symptoms induced by SRS-A in a human subject. The compounds are valuable therefore in the prevention and treatment of such disease states in which SRS-A is the causative factor, e.g. skin disorders, allergic rhinitis, and obstructive airways diseases. The compounds are particularly valuable in the prevention and treatment of allergic bronchial asthma.

A compound of formula I, or a pharmaceutically-acceptable salt thereof, can be administered to a human subject either alone, or, preferably, in combination with pharmaceutically-acceptable carriers or diluents, in a pharmaceutical composition, according to standard pharmaceutical practice. A compound can be administered orally or parenterally. Parenteral administration includes intravenous, intramuscular, intraperitoneal, subcutaneous and topical administration, and also administration by inhalation and insufflation.

In a pharmaceutical composition comprising a compound of formula I, or a pharmaceutically-acceptable salt thereof, the weight ratio of carrier to active ingredient will normally be in the range from 1:6 to 6:1, and preferably 1:2 to 4:1. However, in any given case, the ratio chosen will depend on such factors as the solubility of the active component, the dosage contemplated and the precise route of administration.

For oral use of an SRS-A antagonist of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic. For administration by inhalation or insufflation, it is convenient to prepare an aqueous or partially aqueous solution of a compound of formula I or salt thereof, and then this solution is administered in the form of an aerosol.

When a compound of formula I or salt thereof is used as an SRS-A antagonist in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 0.02 g. to about 1.0 g., and preferably 0.05 g. to 0.5 g., in single or divided doses. On the other hand, it may be necessary to use dosage outside these limits in some cases.

The following examples and preparations are provided solely for the purpose of further illustration. Infrared (IR) spectra were measured as potassium bromide discs (KBr discs), and diagnostic absorption bands are reported in reciprocal centimeters ($cm^{-1}$). Nuclear magnetic resonance spectra (NMR) were measured in deuterochloroform ($CDCl_3$) or perdeutero dimethyl sulfoxide ($DMSO-d_6$), and peak positions are expressed in parts per million (ppm) downfield from internal tetramethylsilane. The following abbreviations for peak shapes are used: s, singlet; b, broad absorption; d, doublet; t, triplet; and m, multiplet. If the term "trans" or "cis" precedes the chemical name of a compound of formula I, IV, V or VI, this indicates the stereochemical relationship of the phenyl group A and the $CONHR^1$ or COOH group across the double bond. Where no such term appears, the compound is of undetermined stereochemistry.

EXAMPLE 1 trans-N-Octyl-2-phenyl-3-(4-[cis-3-carboxypropenamido]phenyl)propenamide

A stirred mixture of 1.6 g. of trans-N-decyl-2-phenyl-3-(4-aminophenyl)propenamide and 25 ml. of toluene was heated on a steam bath until a solution was obtained. To this solution was then added 500 mg. of maleic anhydride and heating and stirring was continued for 10 minutes. The reaction mixture was then cooled, and the solvent was removed by evaporation in vacuo. The resulting residue was induced to solidify by trituration under ether, and the solid thus obtained was recovered by filtration. The solid was recrystallized from acetonitrile to give 1.07 g. of the title compound as a yellow solid, m.p. 104°–105° C. The IR spectrum (KBr disc) showed absorptions at 3310, 2940, 1725 and 1600 $cm^{-1}$.

Anal. Calcd. for $C_{27}H_{32}N_2O_4$: C, 72.29; H, 7.19; N, 6.25%. Found: C, 72.31; H, 7.15; N, 6.22%.

EXAMPLE 2

Reaction of the appropriate N-alkyl-2-phenyl-3-(aminophenyl) or N-alkyl-3-phenyl-3-(aminophenyl) derivative of propenamide from Preparations 9, 10, 11, 25, 26, 27 or 28 with maleic anhydride, succinic anhydride or glutaric anhydride, substantially according to the procedure of Example 1, affords the compounds in the following Table I. In some instances, benzene was used as the solvent rather than toluene. In those cases in which the product was out of solution at the end of the reaction, it was recovered either by filtration or decantation. In those cases in which the product was not out of solution at the end of the reaction, it was recovered by removing the solvent by evaporation in vacuo.

TABLE I

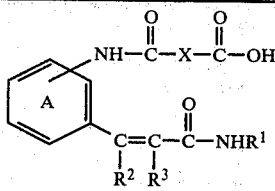

| $R^1$ | $R^2$ | $R^3$ | X | Position of NHCOX-COOH group * | Stereochemistry  | Recrystallization solvent * | Yield | Melting Point (°C.) | Calculating (%) C | H | N | Found (%) C | H | N |
|---|---|---|---|---|---|---|---|---|---|---|---|---|---|---|
| octyl | H | $C_6H_5$ | $-CH_2CH_2-$ | 4 | trans | A | 69 | 140–141 | 71.97 | 7.61 | 6.22 | 72.35 | 7.43 | 6.26 |
| decyl | H | $C_6H_5$ | $-CH=CH-$ | 4 | trans | B | 41 | 134–135 | 73.08 | 7.61 | 5.88 | 72.99 | 7.40 | 5.89 |
| decyl | H | $C_6H_5$ | $-CH_2CH_2-$ | 4 | trans | A | 56 | 127–128 | 72.77 | 8.00 | 5.85 | 72.43 | 7.91 | 5.87 |
| 1-methyldecyl | H | $C_6H_5$ | $-CH=CH-$ | 4 | trans | A | 45 | 144–145 | 73.44 | 7.81 | 5.71 | 73.54 | 7.71 | 5.75 |
| 1-methyldecyl | H | $C_6H_5$ | $-CH_2CH_2-$ | 4 | trans | A | 39 | 98–100 | 73.14 | 8.18 | 5.69 | 73.14 | 8.06 | 5.68 |
| decyl | $C_6H_5$ | H | $-CH=CH-$ | 4 | | A | 37 | 108–110 | 73.08 | 7.61 | 5.88 | 72.96 | 7.53 | 5.94 |
| decyl | $C_6H_5$ | H | $-CH=CH-$ | 3 | cis | A | 50 | 134–136 | 73.08 | 7.61 | 5.88 | 73.09 | 7.58 | 6.16 |
| decyl | $C_5H_5$ | H | $-CH=CH-$ | 3 | trans | A | 53 | 184–185 | 73.08 | 7.61 | 5.88 | 73.01 | 7.66 | 5.98 |
| decyl | $C_6H_5$ | H | $-CH_2CH_2-$ | 4 | | B | 33 | 156–158 | 72.77 | 8.00 | 5.85 | 72.66 | 7.83 | 6.04 |
| decyl | $C_6H_5$ | H | $-CH_2CH_2CH_2-$ | 4 | | B,A | 26 | 126–129 | 73.14 | 8.18 | 5.69 | 72.83 | 7.97 | 5.53 |
| 1-methyldecyl | $C_6H_5$ | H | $-CH=CH-$ | 4 | cis | A | 26 | 151–151.5 | 73.44 | 7.81 | 5.71 | 73.17 | 7.72 | 5.75 |
| 1-methyldecyl | $C_6H_5$ | H | $-CH=CH-$ | 4 | trans | A | 23 | 148–150 | 73.44 | 7.81 | 5.71 | 73.41 | 7.91 | 5.65 |
| 1-methyldecyl | $C_6H_5$ | H | $-CH=CH-$ | 3 | trans | C | 56 | 195(dec) | 73.44 | 7.81 | 5.71 | 73.35 | 7.80 | 5.86 |
| 1-methyldecyl | $C_6H_5$ | H | $-CH=CH-$ | 3 | cis | A | 60 | 148–149 | 73.44 | 7.81 | 5.71 | 73.83 | 7.75 | 5.81 |
| 1-methyldecyl | $C_6H_5$ | H | $-CH_2CH_2-$ | 4 | | B | 37 | 147–149.5 | 73.14 | 8.18 | 5.69 | 73.03 | 8.02 | 5.71 |

*The numeral in this column indicates the position of the NHCOXCOOH group on the phenyl ring A;
the $-\underset{\underset{R^2}{|}}{C}=\underset{\underset{R^3}{|}}{C}-CONHR^1$ group is at the 1-position.

**The entry in this column indicates the stereochemical relationship of the phenyl ring A and the group $CONHR^1$ across the double bond; where no entry appears, the stereochemistry was undetermined.
***Solvent code: A, acetonitrile; B, ethyl acetate; C, glacial acetic acid.

TABLE II
SPECTRAL DATA

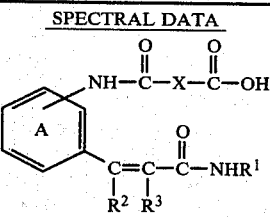

| $R^1$ | $R^2$ | $R^3$ | X | Position of NHCOX-COOH group * | Stereochemistry ** | IR (cm$^{-1}$) (KBr disc) | NMR (ppm) (DMSO-$d_6$) |
|---|---|---|---|---|---|---|---|
| octyl | H | $C_6H_5$ | $-CH_2CH_2-$ | 4 | trans | 2940, 1725, 1655, 1615 | |
| decyl | H | $C_6H_5$ | $-CH=CH$ | 4 | trans | 2940, 1740, 1640, 1615 | |
| decyl | H | $C_6H_5$ | $-CH_2CH_2$ | 4 | trans | 2965, 1725, 1605, 1525 | |
| 1-methyldecyl | H | $C_6H_5$ | $-CH=CH-$ | 4 | trans | 2960, 1720, 1645, 1600 | |
| 1-methyldecyl | H | $C_6H_5$ | $-CH_2CH_2-$ | 4 | trans | 2940, 1710, 1605, 1530 | |
| decyl | $C_6H_5$ | H | $-CH=CH-$ | 4 | | 3335, 2900, 1720, 1630 | 0.90 (m), 1.20 (s), 3.00 (b), 6.40 (d), 7.35 (m), 10.50 (s) |
| decyl | $C_6H_5$ | H | $-CH=CH-$ | 3 | cis | 3280, 2915, 1735, 1670 | 0.90 (m), 1.25 (s), 3.00 (b), 6.35 (d), 7.40 (m), 10.55 (s) |

TABLE II-continued
SPECTRAL DATA

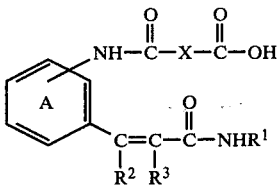

| R[1] | R[2] | R[3] | X | Position of NHCOX-COOH group * | Stereo-chemistry ** | IR (cm$^{-1}$) (KBr disc) | NMR (ppm) (DMSO-d$_6$) |
|---|---|---|---|---|---|---|---|
| decyl | C$_6$H$_5$ | H | —CH=CH— | 3 | trans | 3280, 2915, 1715, 1585 | 0.90 (m), 1.20 (s), 3.00 (b), 6.40 (d), 7.30 (m), 10.55 (s) |
| decyl | C$_6$H$_5$ | H | —CH$_2$CH$_2$— | 4 | | 3300, 2940, 1705, 1665 | 0.90 (m), 1.20 (s), 2.95 (b), 6.35 (s), 7.35 (m), 10.05 (s) |
| decyl | C$_6$H$_5$ | H | —CH$_2$CH$_2$CH$_2$— | 4 | | 2610, 2925, 1720, 1645 | 0.90 (m), 1.20 (s), 1.85 (b), 2.45 (b), 2.95 (m), 6.35 (d), 7.30 (m), 9.95 (s) |
| 1-methyldecyl | C$_6$H$_5$ | H | —CH=CH— | 4 | cis | 3335, 2925, 1720, 1640 | 0.95 (d), 3.65 (b), 6.45 (d), 7.40 (m), 10.60 (s) |
| 1-methyldecyl | C$_6$H$_5$ | H | —CH=CH— | 4 | trans | 3310, 2905, 1725, 1625 | 0.95 (m), 1.20 (s), 3.60 (b), 6.40 (d), 7.33 (m), 10.52 (s) |
| 1-methyl | C$_6$H$_5$ | H | —CH=CH— | 3 | trans | 3310, 2940, 1725, 1560 | 0.90 (d), 1.20 (s), 3.65 (b), 6.38 (t), 7.30 (m), 10.60 (s) |
| 1-methyldecyl | C$_6$H$_5$ | H | —CH=CH— | 3 | cis | 3300, 2925, 1720, 1600 | 0.90 (d), 1.20 (s), 4.15 (b), 6.40 (d), 7.40 (m), 10.55 (s) |
| 1-methyldecyl | C$_6$H$_5$ | H | —CH$_2$CH— | 4 | | 3280, 2905, 1725, 1645 | 0.90 (m), 1.20 (s), 3.65 (b), 6.30 (s), 7.30 (m), 9.95 (s) |

*The numeral in this column indicates the position of the NHCOXCOOH group on the phenyl ring A;

the —C=C—COHNR[1] group is at the 1-position.
      |  |
      R[2] R[3]

**The entry in this column indicates the stereochemical relationship of the phenyl ring A and the group CONHR[1] across the double bond; where on entry appears, the stereochemistry was undetermined.

EXAMPLE 3

Reaction of the appropriate N-alkyl-2-phenyl-3-(aminophenyl)propenamide or N-cycloalkyl-2-phenyl-3-(aminophenyl)propenamide compound from Preparation 12 with maleic anhydride, succinic anhydride or glutaric anhydride, according to the procedure of Example 1, affords the following compounds:
trans-N-tridecyl-2-phenyl-3-(2-[4-carboxybutanamido]phenyl)propenamide,
trans-N-tridecyl-2-phenyl-3-(2-[cis-3-carboxypropenamido]phenyl)propenamide,
trans-N-pentadecyl-2-phenyl-3-(3-[3-carboxypropanamido]phenyl)propenamide,
trans-N-cyclohexyl-2-phenyl-3-(4-[3-carboxypropenamiddo]phenyl)propenamide,
trans-N-cyclodecyl-2-phenyl-3-(2-[cis-3-carboxypropenamido]phenyl)propenamide,
trans-N-cyclodecyl-2-phenyl-3-(2-[4-carboxybutanamido]phenyl)propenamide,
trans-N-cyclododecyl-2-phenyl-3-(3-[3-carboxypropanamido]phenyl)propenamide,
trans-N-cyclododecyl-2-phenyl-3-(3-[cis-3-carboxypropenamido]phenyl)propenamide,
cis-N-octyl-2-phenyl-3-(4-[cis-3-carboxypropenamido]phenyl)propenamide,
cis-N-decyl-2-phenyl-3-(4-[3-carboxypropanamido]phenyl)propenamide,
cis-N-pentadecyl-2-phenyl-3-(4-[4-carboxybutanamido]phenyl)propenamide,
cis-N-cyclohexyl-2-phenyl-3-(4-[cis-3-carboxypropenamido]phenyl)propenamide, and
cis-N-cyclododecyl-2-phenyl-3-(4-[4-carboxybutanamido]phenyl)propenamide.

EXAMPLE 4

Reaction of the appropriate N-alkyl-3-phenyl-3-(aminophenyl)propenamide or N-cycloalkyl-3-phenyl-3-(aminophenyl)propenamide compound from Preparation 29 with maleic anhydride, succinic anhydride or glutaric anhydride, according to the procedure of Example 1, affords the following compounds:
N-octyl-3-phenyl-3-(4-[cis-3-carboxypropenamido]phenyl)propenamide,
N-decyl-3-phenyl-3-(2-[cis-3-carboxypropenamido]phenyl)propenamide,
N-tridecyl-3-phenyl-3-(2-[4-carboxybutanamido]phenyl)propenamide,
N-(11-methyldodecyl)-3-phenyl-3-(3-[cis-3-carboxypropenamido]phenyl)propenamide,
N-pentadecyl-3-phenyl3-(4-[4-carboxybutanamido]phenyl)propenamide,
N-cyclohexyl-3-phenyl-3-(4-[3-carboxypropanamido]phenyl)propenamide,
N-cyclooctyl-3-phenyl-3-(3-[cis-3-carboxypropenamido]phenyl)propenamide,
N-cycloundecyl-3-phenyl-3-(2-[cis-3-carboxypropenamido]phenyl)propenamide,
N-cycloundecyl-3-phenyl-3-(2-[4-carboxybutanamido]phenyl)propenamide, and N-cyclododecyl-3-phenyl-3-(4-[4-carboxybutanamido]-phenyl)propenamide.

PREPARATION 1 cis- and trans-2-Phenyl-3-(4-nitrophenyl)propenoic Acid

A mixture of 75.6 g. of 4-nitrobenzaldehyde, 61.3 g. of 2-phenylacetic acid, 50 ml. of acetic anhydride and 50 ml. of pyridine was heated in an oil bath at 140° C. for 35 minutes. To the cooled mixture was then added about 100 ml. of concentrated hydrochloric acid, followed by sufficient water to give a total volume of 700 ml. The resulting mixture was stirred for 30 minutes and then the precipitate was filtered off. The recovered solid was stirred with 1 liter of 0.5 N sodium hydroxide for 30 minutes, and then the insoluble material was removed by filtration. The filtrate was diluted to 2.5 liters, and the pH was adjusted to 4.5 using glacial acetic acid. The precipitate was removed by filtration to give 50 g. of a yellow solid. Acidification of the filtrate with 100 ml. of concentrated hydrochloric acid caused further solid to precipitate. It was filtered off. It weighed 8.0 g. The solid weighing 50 g. was recrystallized from glacial acetic acid to give 41.0 g. of trans-2-phenyl-3-(4-nitrophenyl)propenoic acid, m.p. 212.5°-213.5° C. The solid weighing 8.0 g. was recrystallized from toluene to give 6.8 g. of cis-2-phenyl-3(4-nitrophenyl)propenoic acid, m.p, 132.5°-133.5° C.

PREPARATION 2

Reaction of either 3-nitrobenzaldehyde or 2-nitrobenzaldehyde with 2-phenylacetic acid, according to the procedure of Preparation 1, affords the following compounds.
trans-2-phenyl-3-(3-nitrophenyl)propenoic acid, and
trans-2-phenyl-3-(2-nitrophenyl)propenoic acid.

PREPARATION 3 trans-2-Phenyl-3-(4-nitrophenyl)propenoyl chloride

To a stirred slurry of 41.0 g. of trans-2-phenyl-3-(4-nitrophenyl)propenoic acid in 300 ml. of toluene was added 22.0 g. of phosphorus trichloride and 2 ml. of N,N-dimethylformamide. The slurry was heated on a steam bath for 30 minutes, an additional 2 ml. of N,N-dimethylformamide was added, and then heating and sitrring on a steam bath was continued for an additional 30 minutes. The reaction mixture was then filtered, and the cooled filtrate was evaporated in vacuo. The residue was triturated with hexane, and the solid which formed was recovered by filtration to give 36 g. of the title compound as a yellow solid. This material was combined with 5.0 g. of material of comparable quality and the combined material was heated at the boiling point in ca. 800 ml. of 1:1 cyclohexane-carbon tetrachloride. The insoluble material was removed by filtration and the volume of the filtrate was reduced to 350 ml. To this concentrated solution was added 100 ml. of hexane and the solid which precipitated was removed by filtration. This afforded 32.5 g. of the title compound as a yellow solid, m.p. 92.5°-93.5° C.

PREPARATION 4

Reaction of the appropriate propenoic acid from Preparation 1 or Preparation 2 with phosphorus pentachloride, according to the procedure of Preparation 3, affords the following acid chlorides:
cis-2-phenyl-3-(4-nitrophenyl)propenoyl chloride,
trans-2-phenyl-3-(3-nitrophenyl)propenoyl chloride, and
trans-2-phenyl-3-(2-nitrophenyl)propenoyl chloride.

PREPARATION 5 trans-N-Octyl-2-phenyl-3-(4-nitrophenyl)propenamide

To a stirred solution of 5.9 g. of octylamine in 30 ml. of tetrahydrofuran, cooled in an ice-bath, was added dropwise a solution of 6.0 g. of trans-2-phenyl-3-(4-nitrophenyl)propenoyl chloride in 40 ml. of tetrahydrofuran, during 20 minutes. Stirring was continued at 25° C. for 45 minutes, and then the solvent was removed in vacuo. The residue was partitioned between 300 ml. of ethyl acetate and 75 ml. of water. The layers were separated and the ethyl acetate solution was washed successively with 1 N hydrochloric acid, water, 1 N potassium hydroxide, water and saturated sodium chloride solution. The ethyl acetate solution was dried ($Na_2SO_4$) and evaporated in vacuo to give 7.0 g. of the title compound as a waxy solid, m.p. 93°-94.5° C.

PREPARATION 6 trans-N-Decyl-2-phenyl-3-(4-nitrophenyl)propenamide

The title compound was prepared from decylamine and trans-2-phenyl-3-(4-nitrophenyl)propenoyl chloride, substantially according to the procedure of Preparation 5. Yield: 97%. M.p.: 95.5°-97.5° C. A small sample was recrystallized from ethanol, to give material having m.p. 100°-101° C. The ultraviolet spectrum of this latter material in ethanol showed an absorption maximum at 315 millimicrons (epsilon, 16,454).

PREPARATION 7 trans-N-(1-Methyldecyl)-2-phenyl-3-(4-nitrophenyl)-propenamide

The title compound was prepared from 1-methyldecylamine and trans-2-phenyl-3-(4-nitrophenyl)propenoyl chloride, substantially according to the procedure of Preparation 5, in essentially quantitative yield. M.p. 71.5°-74° C.

PREPARATION 8

Reaction of the appropriate acid chloride from Preparation 3 or Preparation 4 with the requisite alkylamine or cycloalkylamine, according to the procedure of Preparation 5, affords the following compounds:
trans-N-tridecyl-2-phenyl3-(2-nitrophenyl)propenamide,
trans-N-pentadecyl-2-phenyl-3-(3-nitrophenyl)propenamide,
trans-N-cyclohexyl-2-phenyl-3-(4-nitrophenyl)propenamide,
trans-N-cyclodecyl-2-phenyl-3-(2-nitrophenyl)propenamide,
trans-N-cyclododecyl-2-phenyl-3-(3-nitrophenyl)-propenamide,
cis-N-octyl-2-phenyl-3-(4-nitrophenyl)propenamide,
cis-N-decyl-2-phenyl-3-(4-nitrophenyl)propenamide,
cis-N-pentadecyl-2-phenyl-3-(4-nitrophenyl)propenamide,
cis-N-cyclohexyl-2-phenyl-3-(4-nitrophenyl)propenamide, and
cis-N-cyclododecyl-2-phenyl-3-(4-nitrophenyl)-propenamide.

PREPARATION 9 trans-N-Octyl-2-phenyl-3-(4-aminophenyl)propenamide

To a stirred solution of 7.0 g. of trans-N-octyl-2-phenyl-3-(4-nitrophenyl)propenamide, in 75 ml. of glacial acetic acid, at ca. 85° C., was added 5.0 g. of iron powder, portionwise, during about 15 minutes. The heat of reaction kept the temperature of the reaction mixture between 90° and 95° C. Stirring was continued for 15 minutes, and then the reaction mixture was filtered hot (65° C.). The residue was washed with further glacial acetic acid, and the combined acetic acid solutions were evaporated in vacuo. The residue was partitioned between ethyl acetate and water, and then the ethyl acetate layer was removed. It was washed with water, followed by saturated sodium chloride solution, and then it was dried over sodium sulfate. Evaporation in vacuo gave 6.8 g. of the title compound as an oil.

The above oil was purified by chromatography on silica gel, eluting with chloroform containing 1% of ethanol. This afforded 6.2 g. of the title compound as an oil.

PREPARATION 10 trans-N-Decyl-2-phenyl-3-(4-aminophenyl)propenamide

The title compound was prepared in essentially quantitative yield by the reduction of trans-N-decyl-2-phenyl-3-(4-nitrophenyl)propenamide with iron powder in acetic acid, substantially according to the procedure of Preparation 9, but without chromatographic purification.

PREPARATION 11 trans-N-(1-Methyldecyl)-2-phenyl-3-(4-aminophenyl)propenamide

The title compound was prepared in 83% yield by the reduction of trans-N-(1-methyldecyl)-2-phenyl-3-(4-nitrophenyl)propenamide with iron powder in acetic acid, substantially according to Preparation 9, but without chromatographic purification.

PREPARATION 12

Reduction of the products of Preparation 8 with iron powder in acetic acid, according to the procedure of Preparation 9, affords the following amines:
trans-N-tridecyl-2-phenyl-3-(2-aminophenyl)propenamide,
trans-N-pentadecyl-2-phenyl-3-(3-aminophenyl)propenamide,
trans-N-cyclohexyl-2-phenyl-3-(4-aminophenyl)propenamide,
trans-N-cyclodecyl-2-phenyl-3-(2-aminophenyl)propenamide,
trans-N-cyclododecyl-2-phenyl-3-(3-aminophenyl)propenamide,
cis-N-octyl-2-phenyl-3-(4-aminophenyl)propenamide,
cis-N-decyl-2-phenyl-3-(4-aminophenyl)propenamide,
cis-N-pentadecyl-2-phenyl-3-(4-aminophenyl)propenamide,
cis-N-cyclohexyl-2-phenyl-3-(4-aminophenyl)propenamide, and
cis-N-cyclododecyl-2-phenyl-3-(4-aminophenyl)propenamide.

PREPARATION 13

Ethyl 3-Phenyl-3-(4-nitrophenyl)propenoate

To a stirred suspension of sodium hydride, derived from 10.56 g. of a 50% suspension in mineral oil, in 400 ml. of 1,2-dimethoxyethane was added 51.6 g. of diethyl ethoxycarbonylmethylphosphonate, during 1 hour. When gas evolution ceased, a solution of 47.7 g. of 4-nitrobenzophenone in 400 ml. of 1,2-dimethoxyethane was added, dropwise, during 1.5 hours. Stirring was continued overnight and then the solvent was removed by evaporation in vacuo. The residue was partitioned between ethyl acetate and water. The layers were separated, and the water layer was extracted with fresh ethyl acetate. The combined ethyl acetate solutions were evaporated in vacuo to give the title compound as an oil, which slowly solidified.

PREPARATION 14

Ethyl 3-Phenyl-3-(3-nitrophenyl)propenoate

The title compound was obtained as an oil by condensation of diethyl ethoxycarbonylmethylphosphonate and 3-nitrobenzophenone, using the procedure of Preparation 13.

PREPARATION 15

Ethyl 3-Phenyl-3-(2-nitrophenyl)propenoate

The title compound is obtained by condensation of diethyl ethoxycarbonylmethylphosphonate and 2-nitrobenzaldehyde, using the procedure of Preparation 13.

PREPARATION 16

3-Phenyl-3-(4-Nitrophenyl)propenoic Acid

A mixture of 62.5 g. of ethyl 3-phenyl-3-(4-nitrophenyl)propenoate, 100 ml. of ethanol and 300 ml. of 1.5 N potassium hydroxide was heated on a steam bath for 1 hour. To the cooled reaction mixture was added 800 ml. of water and 500 ml. of ethyl acetate, and then the ethyl acetate layer was removed. The aqueous layer was acidified, and the solid which precipitated was collected by filtration. This solid was recrystallized from toluene and then from carbon tetrachloride to give 22 g. of the title compound, m.p. 188°–189° C.

Anal. Calcd. for $C_{15}H_{11}NO_4$: C, 66.91; H, 4.12; N, 5.20%. Found: C, 66.64; H, 4.24; N, 5.20%.

PREPARATION 17

3-Phenyl-3-(3-nitrophenyl)propenoic Acid

The title compound was obtained by hydrolysis of ethyl 3-phenyl-3-(3-nitrophenyl)propenoate with potassium hydroxide, according to the procedure of Preparation 16. The product precipitated as a gum after acidification of the aqueous phase, and it was isolated by extraction with chloroform. It was recrystallized from toluene-cyclohexane (twice) and carbon tetrachloride, giving 39.4 g. of material melting at 116°–119° C.

PREPARATION 18

3-Phenyl-3-(2-nitrophenyl)propenoic Acid

The title compound is prepared by hydrolysis of ethyl 3-phenyl-3-(2-nitrophenyl)propenoate, using the procedure of Preparation 16.

PREPARATION 19

3-Phenyl-3-(4-nitrophenyl)propenoyl chloride

A mixture of 22 g. of 3-phenyl-3-(4-nitrophenyl)propenoic acid, 11.7 g. of thionyl chloride and 150 ml. of benzene was heated under reflux for 1 hour. The solvent was removed by evaporation in vacuo, and the residual solid was recrystallized from carbon tetrachloride. This afforded 20 g. of the title compound, m.p. 117°–120° C.

PREPARATION 20

N-Decyl-3-phenyl-3-(4-nitrophenyl)propenamide

To a stirred solution of 5.89 g. of decylamine in 25 ml. of tetrahydrofuran was added a solution of 4.89 g. of 3-phenyl-3-(4-nitrophenyl)propenoyl chloride in 25 ml. of tetrahydrofuran, dropwise, during 20 minutes, at ice-bath temperature. The solvent was removed by evaporation in vacuo and the residue was partitioned between ethyl acetate and water. The layers were separated, and the ethyl acetate layer was washed with water, dried using sodium sulfate, and then evaporated in vacuo. This afforded 5.6 g. of the title compound, m.p. 91°–93° C.

PREPARATION 21

N-Decyl-3-phenyl-3-(3-nitrophenyl)propenamide

To a stirred solution of 8.0 g. of 3-phenyl-3-(3-nitrophenyl)propenoic acid in 260 ml. of methylene chloride was added 3.3 g. of triethylamine. The mixture was stirred for 20 minutes and then it was cooled in an ice-bath. To the cooled solution was added, dropwise, during 15 minutes, a solution of 3.6 g. of ethyl chloroformate in 30 ml. of methylene chloride. Stirring was continued for 20 minutes, and then a solution of 5.2 g. of decylamine in 30 ml. of methylene chloride was added, dropwise, during 10 minutes. The reaction mixture was allowed to warm to room temperature, and then it was washed successively with 1 N potassium hydroxide, 1 N hydrochloric acid, water, and saturated sodium chloride solution. The resulting solution was dried ($Na_2SO_4$) and evaporated in vacuo to give the 10.7 g. of the title compound as a oil.

PREPARATION 22

N-(1-Methyldecyl)-3-phenyl-3-(4-nitrophenyl)propenamide

The title compound was prepared from 3-phenyl-3-(4-nitrophenyl)propenoic acid via mixed anhydride formation using ethyl chloroformate, followed by reaction with 1-methyldecylamine, substantially according to the procedure of Preparation 21. The product was induced to solidify by trituration under hexane. The solid was recrystallized from hexane, giving a small amount of material which was discarded. The mother liquors were evaporated in vacuo to give an oil which solidified when stirred under acetonitrile. The solid was filtered off, giving a 51% yield of the title compound, m.p. 69°–71° C.

PREPARATION 23

N-(1-Methyldecyl)-3-phenyl-3-(3-nitrophenyl)propenamide

The title compound was prepared from 3-phenyl-3-(3-nitrophenyl)propenoic acid via mixed anhydride formation using ethyl chloroformate, followed by reaction with 1-methyldecylamine, substantially according to the procedure of Preparation 21. This gave a 92% yield of an oil.

PREPARATION 24

Reaction of the appropriate 3-phenyl-3-(nitrophenyl)propenoic acid with ethyl chloroformate to form a mixed anhydride, followed by reaction of the mixed anhydride with the requisite alkylamine or cycloalkylamine, according to the procedure of Preparation 21, affords the following compounds:
N-Octyl-3-phenyl-3-(4-nitrophenyl)propenamide,
N-decyl-3-phenyl-3-(2-nitrophenyl)propenamide,
N-tridecyl-3-phenyl-3-(2-nitrophenyl)propenamide,
N-(11-methyldodecyl)-3-phenyl-(3-nitrophenyl)propenamide,
N-pentadecyl-3-phenyl-3-(4-nitrophenyl)propenamide,
N-cyclohexyl-3-phenyl-3-(4-nitrophenyl)propenamide,
N-cyclooctyl-3-phenyl-3-(3-nitrophenyl)propenamide,
N-cycloundecyl-3-phenyl-3-(2-nitrophenyl)propenamide, and
N-cyclododecyl-3-phenyl-3-(4-nitrophenyl)propenamide.

PREPARATION 25

N-Decyl-3-phenyl-3-(4-aminophenyl)propenamide

To a stirred solution of 5.6 g. of N-decyl-3-phenyl-3-(4-nitrophenyl)propenamide in 80 ml. of glacial acetic acid, at 85° C., was added, portionwise, during 20 minutes, 3.85 g. of iron powder. The reaction was exothermic and the temperature was between 85° and 90° C. during the addition. After the addition, the reaction mixture was filtered and the solids were washed with further hot acetic acid. The combined acetic acid solutions were evaporated in vacuo and the residue was partitioned between ethyl acetate and water. The ethyl acetate layer was removed, washed with water, and dried. Evaporation in vacuo gave an oil which solidified. The solid was recrystallized from isopropyl ether, giving 2.3 g. of the title compound, m.p. 90°–100° C.

PREPARATION 26

N-Decyl-3-phenyl-3-(3-aminophenyl)propenamide

Reduction of 10.7 g. of N-decyl-3-phenyl-3-(3-nitrophenyl)propenamide with 7.3 g. of iron powder in acetic acid, according to the procedure of Preparation 25, afforded the title compound as an oil. This product was chromatographed on 370 g. of silica gel, eluting with chloroform containing 1% ethanol. This gave 2.2 g. of trans-N-decyl-3-phenyl-3-(3-aminophenyl)propenamide and 0.7 g of cis-N-decyl-3-phenyl-3-(3-aminophenyl)propenamide. The NMR spectrum of the trans-isomer (in $CDCl_3$) showed absorptions at 0.95 (m), 1.25 (s), 3.10 (m), 3.75 (b), 6.35 (s), 6.65 (m) and 7.30 (s) ppm. The NMR spectrum of the cis-isomer (in $CDCl_3$) showed absorptions at 0.90 (m), 1.25 (s), 3.05 (b), 3.65 (b), 5.20 (b), 6.35 (s), 6.65 (m) and 7.15 (m) ppm.

PREPARATION 27

N-(1-Methyldecyl)-3-phenyl-3-(4-aminophenyl)propenamide

Reduction of 6.4 g. of N-(1-methyldecyl)-3-phenyl-3-(4-nitrophenyl)propenamide with 4.2 g. of iron powder in glacial acetic acid, according to the procedure of Preparation 25, afforded the title compound as an oil. This product was chromatographed on 220 g. of silica gel, eluting with 1:1 ethyl acetate-hexane containing 2% triethylamine. This gave 2.0 g. of trans-N-(1-methyldecyl)-3-phenyl-3-(4-aminophenyl)propenamide and 2.5 g. of cis-N-(1-methyldecyl)-3-phenyl-3-(4-aminophenyl)propenamide. The NMR spectrum of the trans-isomer (in $CDCl_3$) showed absorptions at 0.90 (m), 1.20 (s), 3.80 (b), 5.15 (b), 6.30 (s), 6.85 (m) and 7.30 (s) ppm.

The NMR spectrum of the cis-isomer (in $DMSO-d_6$) showed absorptions at 0.95 (m), 1.25 (s), 3.30 (s), 3.75 (b), 5.20 (s), 6.10 (s), 6.70 (m) and 7.30 (m) ppm.

Anal. Calcd. for $C_{26}H_{36}N_2O$: C, 79.56; H, 9.24; N, 7.14%. Found (trans-isomer): C, 79,28; H, 9.57; N, 7.06%. Found (cis-isomer): C, 79.23; H, 9.10; N, 6.97%.

PREPARATION 28

N-(1-Methyldecyl)-3-phenyl-3-(3-aminophenyl)-propenamide

Reduction of 11.6 g. of N-(1-methyldecyl)-3-phenyl-3-(3-nitrophenyl)propenamide with 7.7 g. of iron powder in glacial acetic acid, according to the procedure of Preparation 25, afforded the title compound as an oil. This product was chromatographed on 350 g. of silica gel, eluting with chloroform containing 1% ethanol. This gave 2.3 g. of trans-N-(1-methyldecyl)-3-phenyl-3-(3-aminophenyl)propenamide, 0.25 g. of cis-N-(1-methyldecyl)-3-phenyl-3-(3-aminophenyl)propenamide and 6.2 g. of a mixture of these two isomers. Rechromatography of the mixture afforded a further 0.6 g. of the cis-isomer. The NMR spectrum of the trans-isomer (in $CDCl_3$) showed absorptions at 0.85 (m), 1.25 (s), 3.60 (b), 5.15 (b), 6.35 (s), 6.65 (m) and 7.30 (s) ppm.

The NMR spectrum of the cis-isomer (in $CDCl_3$) showed absorptions at 0.95 (m), 1.30 (s), 3.80 (b), 5.10 (b), 6.55 (s), 6.80 (m) and 7.45 (m) ppm.

PREPARATION 29

Reduction of the products of Preparation 24 with iron powder in acetic acid, according to the procedure of Preparation 25, affords the following amines:
N-octyl-3-phenyl-3-(4-aminophenyl)propenamide,
N-tridecyl-3-phenyl-3-(2-aminophenyl)propenamide,
N-(11-methyldodecyl)-3-phenyl-(3-aminophenyl)-propenamide,
N-pentadecyl-3-phenyl-3-(4-aminophenyl)propenamide,
N-cyclohexyl-3-phenyl-3-(4-aminophenyl)propenamide,
N-cyclooctyl-3-phenyl-3-(3-aminophenyl)propenamide, and
N-cycloundecyl-3-phenyl-3-(2-aminophenyl)propenamide,
N-cyclododecyl-3-phenyl-3-(4-aminophenyl)propenamide.

I claim:

1. A diphenylpropenamide compound of the formula

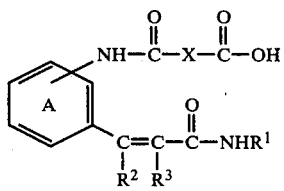

and the pharmaceutically-acceptable salts thereof;
wherein $R^1$ is selected from the group consisting of alkyl having from 8 to 15 carbons and cycloalkyl having from 6 to 12 carbons;
X is selected from the group consisting of cis-vinylene, ethylene and propylene;
and $R^2$ and $R^3$ are each selected from the group consisting of hydrogen and phenyl;
with the proviso that $R^2$ and $R^3$ must always be different.

2. A compound according to claim 1, wherein $R^3$ is phenyl.

3. A compound according to claim 2, wherein the phenyl ring A and the $CONHR^1$ group have a trans relationship across the double bond.

4. A compound according to claim 3, wherein $R^1$ is said alkyl.

5. A compound according to claim 4, wherein X is cis-vinylene.

6. A compound according to claim 5, wherein $R^1$ is octyl, and the two substituents on the phenyl ring A are in a para relationship to each other.

7. A compound according of claim 1, wherein $R^2$ is phenyl.

8. A compound according to claim 7, wherein the phenyl ring A and the $CONHR^1$ group have a trans relationship across the double bond.

9. A compound according to claim 8, wherein $R^1$ is said alkyl.

10. A compound according to claim 9, wherein X is cis-vinylene.

11. A compound according to claim 10, wherein $R^1$ is decyl, and the two substituents on the phenyl ring A are in a para relationship to each other.

12. A compound according to claim 9, wherein X is ethylene.

13. A compound according to claim 12, wherein $R^1$ is 1-methyldecyl, and the two substituents on the phenyl ring A are in a para relationship to each other.

14. A compound according to claim 9, wherein X is propylene.

15. A compound according to claim 14, wherein $R^1$ is decyl, and the two substituents on the phenyl ring A are in a para relationship to each other.

16. A method of antagonizing the effect of slow-reacting substance of anaphylaxis in a human subject, which comprises administering to said human subject a slow-reacting substance of anaphylaxis antagonizing amount of a diphenylpropenamide compound of the formula

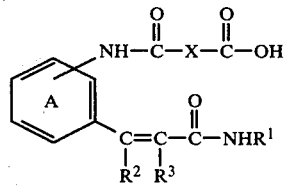

or a pharmaceutically acceptable salt thereof;
wherein $R^1$ is selected from the group consisting of alkyl having from 8 to 15 carbons and cycloalkyl having from 6 to 12 carbons;
X is selected from the group consisting of cis-vinylene, ethylene and propylene;
and $R^2$ and $R^3$ are each selected from the group consisting of hydrogen and phenyl;

with the proviso that R² and R³ must always be different.

17. A pharmaceutical composition, which comprises a pharmaceutically-acceptable carrier and a diphenylpropenamide compound of the formula

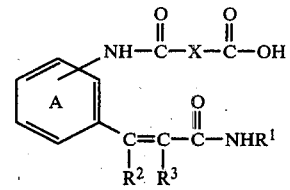

or a pharmaceutically-acceptable salts thereof;

wherein R¹ is selected from the group consisting of alkyl having from 8 to 15 carbons and cycloalkyl having from 6 to 12 carbons;

X is selected from the group consisting of cis-vinylene, ethylene and propylene;

and R² and R³ are each selected from the group consisting of hydrogen and phenyl;

with the proviso that R² and R³ must always be different;

and wherein the ratio of the pharmaceutically-acceptable carrier to the diphenylpropenamide compound is in the range from 1:6 to 6:1 by weight.

* * * * *